United States Patent
Zhou et al.

(10) Patent No.: US 12,134,661 B1
(45) Date of Patent: Nov. 5, 2024

(54) COVALENT MULTI-SPECIFIC ANTIBODY

(71) Applicant: CHIMAGEN BIOSCIENCES, LTD., Sichuan (CN)

(72) Inventors: Zhenhao Zhou, Chengdu (CN); Jie Zhang, Chengdu (CN); Xiaoqing Wang, Chengdu (CN)

(73) Assignee: Chimagen Biosciences, Ltd., Sichuan (CN)

( * ) Notice: Subject to any disclaimer, the term of this patent is extended or adjusted under 35 U.S.C. 154(b) by 0 days.

(21) Appl. No.: 18/668,012

(22) Filed: May 17, 2024

Related U.S. Application Data

(63) Continuation of application No. 17/596,789, filed as application No. PCT/CN2020/087668 on Apr. 29, 2020.

Foreign Application Priority Data

Jun. 20, 2019 (CN) .......................... 201910535703.7

(51) Int. Cl.
   *C07K 16/46* (2006.01)
(52) U.S. Cl.
   CPC ........ *C07K 16/468* (2013.01); *C07K 2317/31* (2013.01); *C07K 2317/56* (2013.01); *C07K 2317/64* (2013.01)
(58) Field of Classification Search
   CPC .............. C07K 16/468; C07K 2317/31; C07K 2317/56
   See application file for complete search history.

(56) References Cited

FOREIGN PATENT DOCUMENTS

| | | |
|---|---|---|
| CN | 106573050 | 4/2017 |
| CN | 109706163 | 5/2019 |
| EP | 2647707 | 10/2013 |
| WO | 2013/026833 | 2/2013 |
| WO | 2015/073721 | 5/2015 |
| WO | 2016/048938 | 3/2016 |
| WO | 2017/055314 | 4/2017 |
| WO | 2018/158719 | 9/2018 |
| WO | 2019/120245 | 6/2019 |
| WO | 2019/179627 | 9/2019 |

OTHER PUBLICATIONS

Extended European Search Report for Co-Pending EP Application No. 20826093.5, dated Jul. 13, 2023, 21 pages.
Seifert et al. "Diabody-Ig: a novel platform for the generation of multivalent and multispedfic antibody molecules" 2019, vol. 11, No. 5, 919-929 https://do!.org/10.1080/19420862.2019.1603024, 11 pages.
Ellwanger, et al. "Redirected optimized cell killing (ROCK®): A highly versatile multispecific fit-for-purpose antibody platform for engaging innate immunity" MABS, vol. 11, No. 5, Jun. 7, 2019 (Jun. 7, 2019) 21 pages.
Klein, et al. "Progress in overcoming the chain association issue in bispecific heterodimeric IgG antibodies" MABS, vol. 4, No. 6, Nov. 1, 2012 (Nov. 1, 2012) 11 pages.
Igawa, et al. "VH/VL interface engineering to promote selective expression and inhibit conformational isomerization of thrombopoietin receptor agonist single chain diabody" Protein Engineering, Design & Selection vol. 23 No. 8, 2010 Published online Jun. 24, },010 11 pages.
Zhu et al "Remodeling domain interfaces to enhance heterodimer formation" Protein Science, vol. 6, No. 4, Apr. 1, 1997. 9 pages.
Bluemel et al. "Epitope distance to the target cell membrane and antigen size determine the potency of T cell-mediated lysis by BiTE antibodies specific for a large melanoma surf ace antigen" Cancer Immunology, Immunotherapy, vol. 59, No. 8, Mar. 23, 2010, 13 pages.
Roda-Navarro, et al. "Understanding the Spatial Topology of Artificial Immunological Synapses Assembled in T Cell-Redirecting Strategies: A Major Issue in Cancer Immunotherapy" Frontiers in Cell and Developmental Biology, vol. 7, Jan. 10, 2020 5 pages.
Dickopf, et al. "Format and geometries matter: Structure-based design defines the functionality of bispecific antibodies" Computational and Structural Biotechnology Journal, vol. 18, May 14, 2020, 7 pages.
Translated International Search Report and Written Opinion for PCT/CN2020/087668, dated Apr. 29, 2020, 8 pages.

*Primary Examiner* — Dong Jiang
(74) *Attorney, Agent, or Firm* — Perkins Coie LLP

(57) ABSTRACT

Disclosed herein are novel bispecific and tri-specific antibodies with increased stability and use thereof for therapy.

1 Claim, 7 Drawing Sheets

Specification includes a Sequence Listing.

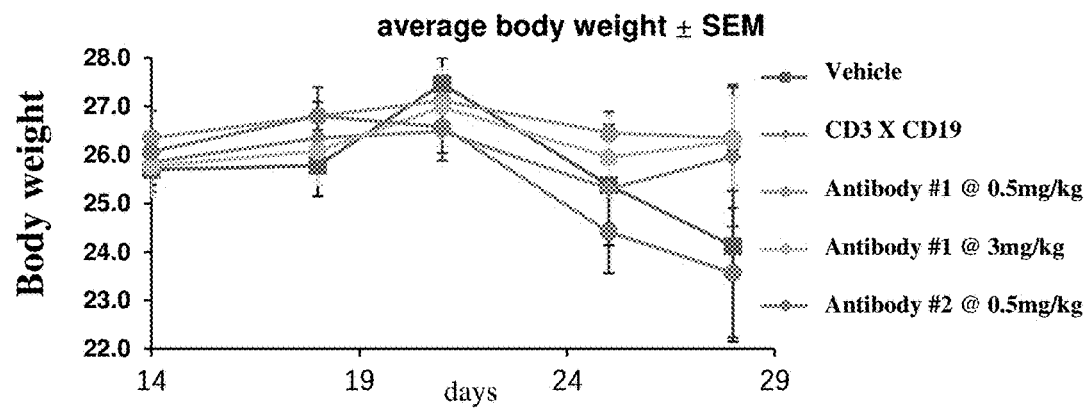
Figure 9
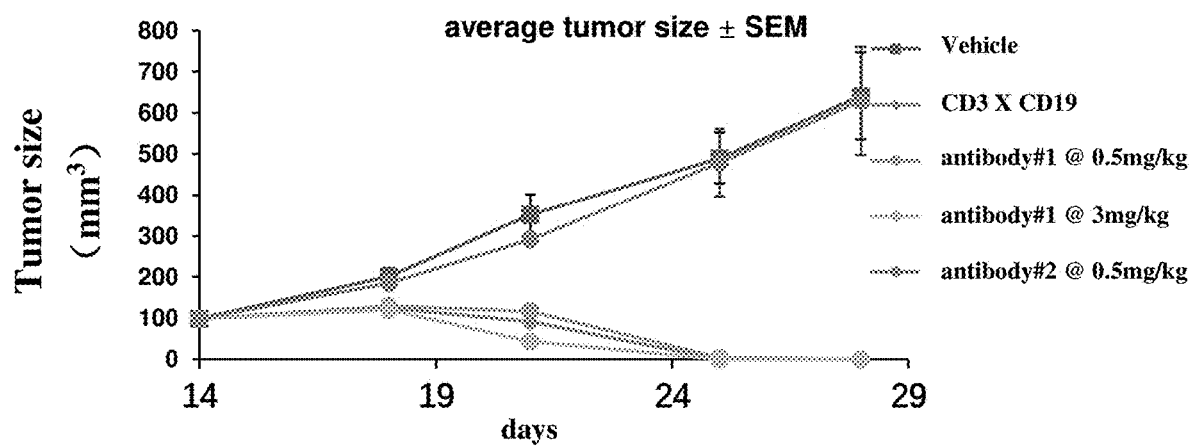

COVALENT MULTI-SPECIFIC ANTIBODY

CROSS REFERENCE TO RELATED APPLICATIONS

The present application is a continuation of U.S. patent application Ser. No. 17/596,789, entitled "COVALENT MULTI-SPECIFIC ANTIBODIES", filed on Dec. 17, 2021, which is a U.S. National Phase Application of International Patent Application Serial No. PCT/CN2020/087668, entitled "COVALENT MULTI-SPECIFIC ANTIBODIES", filed on Apr. 29, 2020, which claims the benefit of, and priority to, Chinese Patent Application Serial No. 201910535703.7, entitled "COVALENT MULTI-SPECIFIC ANTIBODIES", filed on Jun. 20, 2019, the disclosures of which are incorporated by reference in their entireties.

SEQUENCE LISTING

This application contains an ST.26 compliant Sequence Listing, which was submitted in xml format via Patent Center and is hereby incorporated by reference in its entirety. The .xml copy, created on May 17, 2024 is named Sequence Listing XML 1503938002US01.xml and is 32 KB in size.

FIELD OF THE INVENTION

The present invention relates to novel covalent multi-specific antibodies with increased stability and use thereof for therapy.

BACKGROUND OF THE INVENTION

Monoclonal antibodies (mAbs) have wide diagnostic and therapeutic potentials in clinical practices against cancer and other diseases. Monoclonal antibodies play a central role in cancer immunotherapy, either in naked forms, or as conjugates to cytotoxic agents, such as radioisotopes, drugs, toxins, or prodrug-converting enzymes. These approaches are under active evaluation, with different levels of developmental and clinical successes. Naked mAbs potentially may achieve clinical responses by inducing a cytotoxic effect upon binding to cell surface proteins that are over-expressed on cancer cells. Studies have shown that these therapeutic effects were accomplished by controlling tumor growth via programmed cell death (apoptosis), or by the induction of anti-tumor immune responses.

Because of its unique features of specific targeting and mediating effector functions, antibody was explored as drug for targeting immunotherapy against diseases since the invention of monoclonal antibody technology by Cesar Milstein and Georges J. F. Kohler in 1975. There are currently more than 60 approved antibody-based biologic drugs with global annual sales above $50 billion. The successful application of the current generation of antibody drugs has shaped the pharmaceutical industry and has been greatly improving public health. The development of optimal combinational therapies and innovative bi-specific antibodies, in addition to the development of antibody drugs against novel targets, are among the perspective future directions.

Therapeutic antibodies have been used in clinical applications for over twenty years. Currently, there are many anti-tumor antibody drugs in clinic, including Rituxan (1997), Herceptin (1998), Mylotarg (2000), Campath (2001), Zevalin (2002), Bexxer (2003), Avastin (2004), Erbitux (2004), Vectibix (2006), Arzerra (2009); Benlysta (2011); Yervoy (2011), Adcetris (2011), Perjeta (2012), Kadcyla (2013), Opdivo (2014), Keytruda (2014), Tecentriq (2016). These antibodies target mainly EGFR, Her2, CD20 or VEGF, and more recently PD1 or PD-L1.

Multi-functional antibodies are constructed based on traditional antibodies through sophisticated design and molecular engineering, which enable the antibodies to bind to more than one antigen. Practically one single molecule is capable of delivering the same therapeutic effects as that from a combination of several conventional antibodies. However, the advantages of multi-functional antibodies go beyond the simple additive effect of multiple conventional antibodies. Simultaneous engagement of multiple targets of selection can deliver benefits superior to classic antibodies via novel and unique mechanisms. For example, Blinatumomab (CD3×CD19, Amgen) that targets CD3 and CD19 can efficiently engage T cells in the killing of CD19-expressing tumor cells via its CD3-regconizing Fv and show superior efficacy over conventional antibodies in treating ALL (acute lymphoid leukemia) etc. Blinatumomab was approved to launch for ALL treatment by FDA in 2014.

Bispecific antibodies have been produced by chemical cross-linking, by hybrid-hybridomas or transfectomas, or by disulfide exchange at the hinge of two different Fab'. The first method yields heterogeneous and ill-defined products. The second method requires extensive purification of the bispecific antibodies from many hybrid-antibody side products, the presence of which may interfere with the cell cross-linking activity. The disulfide exchange method applies essentially only to $F(ab')_2$ and is thus limited by the susceptibility of the monoclonal antibodies to cleavage by enzyme digestion. Further, since Fab' has little affinity for each other, very high protein concentration is required for the formation of the inter-Fab' disulfide bonds. The disulfide exchange method has been improved by the use of Ellman's reagent to modify one of the Fab' prior to oxidation with the other Fab', reducing the incidence of homodimerization. However, even with this improvement, heterodimeric $F(ab')_2$ can rarely be produced in better than 50% yield. However, adverse safety issues, low response rate and limited effectiveness are general reality of the current antibody drugs. These disadvantages can be from off-target effect to normal tissues/cells because the antibody's epitope is from self antigen, inhibitory microenvironment for immune effector cells, unexpected Fc-mediated effector functions, etc. Thus, there remains a significant need for multi-specific (such as tri-specific) antibodies with excellent therapeutical effect and high purity.

SUMMARY OF THE INVENTION

In the first aspect of the present invention, the present invention provides an engineered antibody, comprising:
  (i) a first polypeptide that, from N-terminal to C-terminal, comprises a second light chain variable domain (VL2) binding a second target and a first heavy chain variable domain (VH1) binding a first target, wherein the VL2 is linked to the VH1 via a linker,
  (ii) a second polypeptide that, from N-terminal to C-terminal, comprises a first light chain variable domain (VL1) binding a first target and a second heavy chain variable domain (VH2) binding a second target, as well as a cysteine-containing hinge domain and a CH2-CH3 domain of IgG, wherein the VL1 is linked to the VH2 via a linker, (iii) a third polypeptide that, from N-terminal to C-terminal, comprises a cysteine-containing hinge domain and a CH2-CH3 domain of IgG;

wherein:

VL1 and VH1 associate to form a domain capable of binding the first target which is CD3;

VL2 and VH2 associate to form a domain capable of binding the second target which is CD19;

VL2 is covalently linked to VH2 via a disulfide bond and VL2 and VH2 independently comprise one or more substitutions that introduce charged amino acids that are electrostatically unfavorable to homodimer formation;

the cysteine-containing hinge domain of the second polypeptide and the cysteine-containing hinge domain of the third polypeptide are covalently linked via a disulfide bond.

In one embodiment of the engineered antibody according to the first aspect, the amino acid sequence of VL1 is SEQ ID NO.:1, the amino acid sequence of VH1 is SEQ ID NO.:2, the amino acid sequence of VL2 is SEQ ID NO.:3, the amino acid sequence of VH2 is SEQ ID NO.:4. The amino acid sequence of the first polypeptide is SEQ ID NO.:5. The amino acid sequence of the second polypeptide is SEQ ID NO.:6. The amino acid sequence of the third polypeptide is SEQ ID NO.:7.

In the second aspect of the present invention, the present invention provides an engineered antibody, comprising:

(i) a first polypeptide that, from N-terminal to C-terminal, comprises a second light chain variable domain (VL2) binding a second target and a first heavy chain variable domain (VH1) binding a first target, wherein the VL2 is linked to the VH1 via a linker, (ii) a second polypeptide that, from N-terminal to C-terminal, comprises a first light chain variable domain (VL1) binding a first target and a second heavy chain variable domain (VH2) binding a second target, as well as a cysteine-containing hinge domain and a CH2-CH3 domain of IgG, wherein the VL1 is linked to the VH2 via a linker, (iii) a third polypeptide that, from N-terminal to C-terminal, comprises a third heavy chain variable domain (VH3) binding a third target, CH1 domain of IgG, a cysteine-containing hinge domain and a CH2-CH3 domain of IgG, wherein the VH3 is linked to CH1 via a linker; and (iv) a fourth polypeptide that, from N-terminal to C-terminal, comprises a third light chain variable domain (VL3) binding the third target, a cysteine-containing CL domain, wherein the VL3 is linked to CL via a linker;

wherein:

VL1 and VH1 associate to form a domain capable of binding the first target;

VL2 and VH2 associate to form a domain capable of binding the second target;

VL3 and VH3 associate to form a domain capable of binding the third target;

VL2 is covalently linked to VH2 via a disulfide bond and VL2 and VH2 independently comprise one or more substitutions that introduce charged amino acids that are electrostatically unfavorable to homodimer formation;

CH1 is covalently linked to CL via a disulfide bond;

the cysteine-containing hinge domain of the second polypeptide and the cysteine-containing hinge domain of the third polypeptide are covalently linked via a disulfide bond.

In one embodiment of the engineered antibody according to the second aspect, the first target is CD3, the second target is CD19 and the third target is CD20. The amino acid sequence of VL1 is SEQ ID NO.:1, the amino acid sequence of VH1 is SEQ ID NO.:2, the amino acid sequence of VL2 is SEQ ID NO.:3, the amino acid sequence of VH2 is SEQ ID NO.:4, the amino acid sequence of VL3 is SEQ ID NO.:8, the amino acid sequence of VH3 is SEQ ID NO.:9. The amino acid sequence of the first polypeptide is SEQ ID NO.:10, the amino acid sequence of the second polypeptide is SEQ ID NO.:11, the amino acid sequence of the third polypeptide is SEQ ID NO.:12 and the amino acid sequence of the fourth polypeptide is SEQ ID NO.:13.

In one embodiment of the engineered antibody according to the second aspect, the first target is CD20, the second target is CD19 and the third target is CD3. The amino acid sequence of VL1 is SEQ ID NO.:8, the amino acid sequence of VH1 is SEQ ID NO.:9, the amino acid sequence of VL2 is SEQ ID NO.:3, the amino acid sequence of VH2 is SEQ ID NO.:4, the amino acid sequence of VL3 is SEQ ID NO.:1, the amino acid sequence of VH3 is SEQ ID NO.:2. The amino acid sequence of the first polypeptide is SEQ ID NO.:14, the amino acid sequence of the second polypeptide is SEQ ID NO.:15, the amino acid sequence of the third polypeptide is SEQ ID NO.:16 and the amino acid sequence of the fourth polypeptide is SEQ ID NO.:17.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 depicts the effect of antibodies #1 and #2 as described herein on mice body weight at different concentrations.

FIG. 9 depicts the inhibition effect of antibodies #1 and #2 as described herein on tumor.

DETAILED DESCRIPTION OF THE INVENTION

Figure 1:
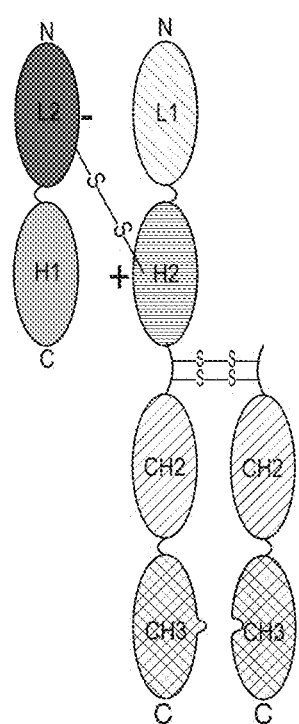
FIG. 1 is the structure diagram of the bispecific antibody according to one embodiment as described herein.

In general, the present invention provides bispecific and tri-specific engineered antibodies that comprise a disulfide bond between VH and VL, mutations on the selected amino acids according to the electrostatic properties thereof and a knob-in-hole structure in Fc segment.

In the first aspect of the present invention, provided is a bispecific engineered antibody, comprising:
(i) a first polypeptide that, from N-terminal to C-terminal, comprises a second light chain variable domain (VL2) binding a second target and a first heavy chain variable domain (VH1) binding a first target, wherein the VL2 is linked to the VH1 via a linker,
(ii) a second polypeptide that, from N-terminal to C-terminal, comprises a first light chain variable domain (VL1) binding a first target and a second heavy chain variable domain (VH2) binding a second target, as well as a cysteine-containing hinge domain and a CH2-CH3 domain of IgG, wherein the VL1 is linked to the VH2 via a linker,
(iii) a third polypeptide that, from N-terminal to C-terminal, comprises a cysteine-containing hinge domain and a CH2-CH3 domain of IgG;
wherein:
VL1 and VH1 associate to form a domain capable of binding the first target which is CD3;
VL2 and VH2 associate to form a domain capable of binding the second target which is CD19;
VL2 is covalently linked to VH2 via a disulfide bond and VL2 and VH2 independently comprise one or more substitutions that introduce charged amino acids, which are electrostatically unfavorable to homodimer formation;
the cysteine-containing hinge domain of the second polypeptide and the cysteine-containing hinge domain of the third polypeptide are covalently linked via a disulfide bond.

In some embodiment according to the first aspect, the first polypeptide from N-terminal to C-terminal has a structure of VL2-linker-VH1.

In some embodiment according to the first aspect, the second polypeptide from N-terminal to C-terminal has a structure of VL1-linker-VH2-hinge-CH2-CH3.

In some embodiment according to the first aspect, the third polypeptide from N-terminal to C-terminal has a structure of hinge-CH2-CH3.

The linkers of the first, the second and the third polypeptides have the sequence of RTVAA, or GGGGS, or GGSGGS, or GGSGGSGGS.

The cysteine-containing hinge domains of the second and the third polypeptides comprise the hinges from IgG1, IgG2, IgG3, IgG4 or IgA.

In one illustrative embodiment according to the first aspect, VL2 comprises a replacement of Gln100 with Cys and a replacement of Gln38 with Lys. VH2 comprises a replacement of Gln39 with Asp, a replacement of Gly44 with Cys. One of the CH3 domains in the second and the third polypeptides comprises a replacement of Thr366 with Trp, and the other CH3 domain comprises replacements of Thr366, Leu368 and Tyr407 with Ser, Ala and Val.

The bispecific antibody as described herein is able to recognise two antigens, and has a disulfide bond and mutations on the selected amino acids according to the electrostatic properties thereof. In some embodiments according to the first aspect, CH2CH3 domains of the second and the third polypeptides form a knob-in-hole structure.

In the second aspect of the present invention, provided is a tri-specific engineered antibody, comprising:
(i) a first polypeptide that, from N-terminal to C-terminal, comprises a second light chain variable domain (VL2) binding a second target and a first heavy chain variable domain (VH1) binding a first target, wherein the VL2 is linked to the VH1 via a linker,
(ii) a second polypeptide that, from N-terminal to C-terminal, comprises a first light chain variable domain (VL1) binding a first target and a second heavy chain variable domain (VH2) binding a second target, as well as a cysteine-containing hinge domain and a CH2-CH3 domain of IgG, wherein the VL1 is linked to the VH2 via a linker,
(iii) a third polypeptide that, from N-terminal to C-terminal, comprises a third heavy chain variable domain (VH3) binding a third target, CH1 domain of IgG, a cysteine-containing hinge domain and a CH2-CH3 domain of IgG, wherein the VH3 is linked to CH1 via a linker, and
(iv) a fourth polypeptide that, from N-terminal to C-terminal, comprises a third light chain variable domain (VL3) binding the third target, a cysteine-containing CL domain, wherein the VL3 is linked to CL via a linker;
wherein:
VL1 and VH1 associate to form a domain capable of binding the first target;
VL2 and VH2 associate to form a domain capable of binding the second target;
VL3 and VH3 associate to form a domain capable of binding the third target;
VL2 is covalently linked to VH2 via a disulfide bond and VL2 and VH2 independently comprise one or more substitutions that introduce charged amino acids, which are electrostatically unfavorable to homodimer formation;
CH1 is covalently linked to CL via a disulfide bond;
the cysteine-containing hinge domain of the second polypeptide and the cysteine-containing hinge domain of the third polypeptide are covalently linked via a disulfide bond.

In some embodiments according to the second aspect, the first polypeptide from N-terminal to C-terminal has a structure of VL2-linker-VH1.

In some embodiments according to the second aspect, the second polypeptide from N-terminal to C-terminal has a structure of VL1-linker-VH2-hinge-CH2-CH3.

In some embodiments according to the second aspect, the third polypeptide from N-terminal to C-terminal has a structure of VH3-linker-CH1-hinge-CH2-CH3.

In some embodiments according to the second aspect, the fourth polypeptide from N-terminal to C-terminal has a structure of VL3-linker-CL.

The linkers of the first, the second, the third and the fourth polypeptides have a sequence of RTVAA, or GGGGS, or GGSGGS, or GGSGGSGGS.

The cysteine-containing hinge domains of the second and the third polypeptides comprise the hinges from IgG1, IgG2, IgG3, IgG4 or IgA.

In one illustrative embodiment according to the second aspect, VL2 comprises a replacement of Gln100 with Cys and a replacement of Gln38 with Lys. VH2 comprises a replacement of Gln39 with Asp, a replacement of Gly44 of Cys. One of the CH3 domains in the second and the third polypeptides comprises a replacement of Thr366 with Trp, and the other CH3 domain comprises replacement of Thr366, Leu368 and Tyr407 with Ser, Ala and Val.

The tri-specific antibody as described herein is able to recognise three antigens, and has a disulfide bond between VH and VL and mutations on the selected amino acids according to the electrostatic properties thereof. In some embodiments according to the second aspect, CH2CH3 domains of the second and the third polypeptides form a knob-in-hole structure.

Disulfide Bond

In some embodiments as described herein, VL2 is covalently linked to VH2 via a disulfide bond. In some embodiments as described herein, FR in VL2 is covalently linked to FR in VH2 via a disulfide bond. Cysteine mutations could be introduced to VL-VH interface to form disulfide bonds between VL and VH, such that VL and VH are covalently linked, thereby improving the stability of the antibodies.

The position 100 of VL2 and the position 44 of VH2 are substituted with cysteine. The substituted cysteines form disulfide bonds that linked VL2 and VH2 of the bispecific and tri-specific antibodies provided herein.

Substitution with Charged Amino Acids

In addition to introduction of a disulfide bond between VL2 and VH2, VL2 and VH2 of the bispecific and tri-specific antibodies as provided herein have one or more amino acids substitutions with different charge properties.

Earlier research showed that the introduction of disulfide bonds substantially improved the stability of the antibodies. However, there was still a portion of heavy and light chains paired up in a non-covalent manner, which has influence on purity. In the tri-specific antibody as provided herein, considering the influence from regional electrostatic forces, one or more amino acids substitutions with different charge properties are introduced to VH2 and VL2, such that the undesirable non-covalent combination will be minimized so as to further improve the stability and purity of the antibodies.

In some embodiments, VL2 is substituted with a negatively charged amino acid, VH2 is substituted with a positively charged amino acid. In some embodiments, VL2 is substituted with a positively charged amino acid, VH2 is substituted with a negatively charged amino acid. The negatively charged amino acid is aspartic acid (D) or glutamic acid (E), and the positively charged amino acid is lysine (K) or arginine (R).

In one illustrative embodiment as described herein, Gln38 of VL2 is substituted with Lys, and Gln39 of VH2 is substituted with Asp, so as to form substitution with charged amino acids.

Knobs-into-Holes Structure

In the bispecific and tri-specific antibodies as provided herein, the hinge domains of the second and the third polypeptides are covalently linked via a disulfide bond. In some embodiments, the CH2CH3 domains of the second and the third polypeptides form a knobs-into-holes structure.

A knobs-into-holes structure, also known as "protuberance-into-cavity" strategy, serves to engineer an interface between a second and third polypeptide for hetero-oligomerization.

In general, the preferred interface comprises at least a part of the CH3 domain of an antibody constant domain. "Protuberances" are constructed by replacing small amino acid side chains from the interface of the second polypeptide with larger side chains (e.g. tyrosine or tryptophan). Compensatory "cavities" of identical or similar size to the protuberances are optionally created on the interface of the third polypeptide by replacing large amino acid side chains with smaller ones (e.g. alanine or threonine). Where a suitably positioned and dimensioned protuberance or cavity exists at the interface of either the second or third polypeptide, it is only necessary to engineer a corresponding cavity or protuberance, respectively, at the adjacent interface. See U.S. Pat. No. 8,216,805, the disclosure of which is incorporated by reference in its entirety.

In one illustrative embodiment as described herein, the CH3 domain of the second polypeptide comprises a replacement of Thr366 with Trp, and the CH3 domain of the third polypeptide comprises replacements of Thr366, Leu368 and Tyr407 with Ser, Ala and Val, such that a knobs-into-holes structure is formed.

In another illustrative embodiment as described herein, the CH3 domain of the second polypeptide comprises replacements of Thr366, Leu368 and Tyr407 with Ser, Ala and Val, and the CH3 domain of the third polypeptide comprises a replacement of Thr366 with Trp, such that a knobs-into-holes structure is formed.

Preparation of the Antibodies

All of the antibody formats are based on heavy chain and light chain of an IgG antibody and can be manufactured by using methods known in the art, which typically include steps of construction of expression cassette for the heavy and light chain genes, co-transfection of the two genes into a suitable cell system to produce the recombinant antibody and to make a stable and high-productive cell clone, cell fermentation to produce cGMP final antibody product.

EXAMPLES

The present invention is further exemplified, but not limited, by the following and Examples that illustrate the preparation of the compounds of the invention.

Example 1. Construction of the Bispecific Antibody

This example illustratively describes the method for constructing a CD3×CD19 bispecific antibody. In the construction of the bispecific antibody, the amino acid sequences of VH and VL of CD3 and CD19 are listed in SEQ ID NOs.: 1 to 4 (CD3 VL: SEQ ID NO.:1, CD3 VH: SEQ ID NO.:2, CD19 VL: SEQ ID NO.:3, CD19 VH: SEQ ID NO.:4).

Construction method. Sequences were optimized for codons using OptimumGene before being synthesized. Target genes were initially constructed in pUC57 vectors and then sub-cloned into pTGE5 vectors. DNAs for transfection were prepared by Maxipreps. CHO3E7 cells were cultured and passed at $0.3 \times 10^6$ cell/ml. Transfection was conducted when cell density reached $1.8$-$2.5 \times 10^6$ cells/ml. 300 μl of DNAs for heavy and light chains, respectively, were first added to 50 ml of Freestyle CHO culture medium and gently mixed. 3 mg of PEI transfection reagent was added later and gently mixed for more than 3 minutes. The mixture was allowed to settle at 37° C. for 7 minutes before being added to 450 ml of cell suspension, making a total volume of 500 ml. 24 hours later, 25 ml of TN1 stock (200 g/L) was added to the mixture. 1 ml of suspension was taken for examination at days 1, 3 and 5 respectively post transfection. 50 μl of each sample was used for cell counting, and the rest was centrifuged for 5 minutes at 3000 rpm before the supernatant was kept at −20° C. On day 6, the culture was harvested and centrifuged for 30 minutes at 5500 rpm. Supernatant was separated, filtered through a 0.22 μm filter and further purified for proteins. Columns: 5 ml Monofinity A Resin (GenScript, Cat. No. L00433) column; Balancing Buffer A: 20 mM PB, 150 mM NaCl, pH7.2; Washing Buffer B: 50 mM citric acid, pH3.5; Neutralizing Buffer C: 1M Tris-HCl, pH9.0; Flow: 2 ml/min; Gradient: 100% gradient wash. Post fractionation, 0.155 ml of Neutralizing Buffer C was added to each 1ml fraction. Collected protein solution was dialyzed in PBS, pH7.2 for 16 hours at 4° C.

CD3×CD19 bispecific antibody (antibody A, whose structure diagram is shown in FIG. 1) comprising three polypeptides as shown below was constructed according to the above-mentioned method.

First polypeptide (SEQ ID NO.: 5): CD19 VL-linker-CD3 VH
Second polypeptide (SEQ ID NO.: 6): CD3 VL-linker-CD19 VH-hinge-CH2CH3
Third polypeptide (SEQ ID NO.: 7): hinge-CH2CH3

The antibody A was purified by Size Exclusion with purity above 95%.

Example 2 Affinity Assay

The affinity of antibody A for human CD3ε antigen and human CD19 antigen was tested by using BIAcore method to calculate ka, kd and KD values. Human CD19 as ligands was immobilized to chips conjugated with anti-histine antibodies. Sample antibodies, at 5 different concentrations, were injected to the system to be analyzed. Human CD3E antigen and human CD19 antigen were immobilized to the chip to assay the affinity of antibody A by using BIAcore method. The results were listed as below.

| Antigen | ka (1/Ms) | kd (1/s) | KD (M) |
|---------|-----------|----------|--------|
| CD3 | 4.876E+5 | 0.01530 | 3.137E−8 |
| CD19 | 3.653E+5 | 6.686E−4 | 1.830E−9 |

Example 3. Cell Killing Assays on Raji Cells

Antibody-mediated killing effect on target cells (Raji cells) was assayed using lymphocytes as effector cells. Protocol as described below.

Preparation of effector cells: Peripheral blood mononuclear cells (PBMCs) were freshly separated from blood through density gradient centrifugation, and CD4+T cells and CD8+T cells were further separated from PBMCs by using Stemcell separation kit. PBMCs, CD4+T cells and CD8+T cells were respectively re-suspended in cell culture medium and cell density and cell survival rate were examined. Cell culture medium was used to adjust cell density to $6×10^6$ live cells/mL before 50 μL per well of cell suspension was added to flat-bottom 96-well plates. Effector cells to target cells ratio (E/T) was 20:1 for the experiments. The cell culture medium was RPMI 1640 in which 10% HI-FBS and 1% Penicillin & Streptomycin were suspended.

Preparation of target cells: Raji cells were passed at $2×10^5$ cells/mL and used for experiments 4 days after passage. Proper amount of cell suspension was transferred to 50 ml tubes and centrifuged for 5 minutes at 200 g, room temperature. Cells were re-suspended with cell culture medium and examined for cell density and cell survival rate. Cell culture medium was used to adjust cell density to $3×10^5$ live cells/mL before 50 μL per well of cell suspension was added to flat-bottom 96-well plates with Raji cells already in.

Preparation of antibodies: The antibody A and blinatumomab, MGD011 and RG6026 as control were diluted to different concentrations in the cell culture medium. 50 μL cell culture medium or diluted solution were added to the indicated wells to arrive at final concentration 0 pM, 1 pM or 100 pM.

Figure 2:
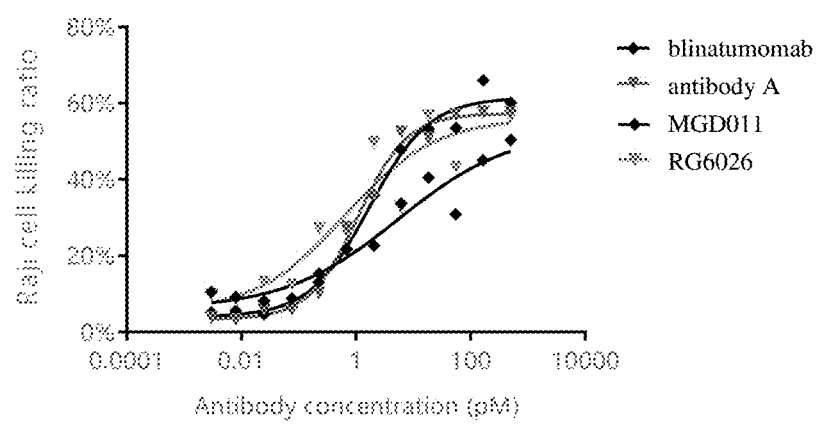
FIG. 2 depicts killing effect of antibody A as described herein on Raji cells.

The 96-well plates with antibodies, target cells and effector cells were placed into an incubator at 37° C. and 5% $CO_2$. At 4-hour point, 20-hour point and 40-hour point, the samples were collected for examination. The samples were centrifuged for 5 minutes at 350 g. The cells were resuspended and stained with PI. 10 μL counting beads were added to each well before conducting flow cytometry. The results showed that antibody A had a EC50 value of 1.086 pM, blinatumomab had a EC50 value of 5.476 pM, MGD011 had a EC50 value of 1.721 pM, RG6026 had a EC50 value of 0.6701 pM. The killing effect of antibody A on target cells was shown in FIG. 2.

Example 3. Evaluation of In Vivo Efficiency

Antibody A was tested for its in vivo anti-tumor effect in Jeko-1/NCG Mixeno model. On the starting day (Day 0), $5×10^6$ Jeko-1 cells suspended in 100 μL 1:1 PBS/gel was inoculated in the right flank of animals. 3 days after inoculation (Day 3) $1×10^7$/0.1 mL PBMC were injected into the abdomen of animals. Sample antibodies were administrated when average tumor size reached 100 mm$^3$. 4 antibodies were tested (blinatumomab@0.5 mg/kg, antibody A@0.3 mg/kg, MGD011@0.3 mg/kg, and RG6026@0.7 mg/kg) together with one pH6.0 PBS control group; 6 animals per group. All samples were administrated by intravenous injection into the caudal vein. All antibodies and the vehicle were administrated twice a week for 3 weeks consecutively. Effect was evaluated based on relative tumor inhibition (TGIRTV), and safety was evaluated on animal weight change and animal death.

Relative tumor growth inhibition rate TGIRTV (%): TGIRTV=1−TRTV/CRTV(%). TRTV/CRTV(%) is relative tumor growth rate, i.e. at a certain time point, the ratio between the tumor volume of the group that received treatment to the tumor volume of the control group that received PBS. TRTV and CRTV are tumor volume (TV) of the treatment group and the control group at a certain time point, respectively.

Figure 3:
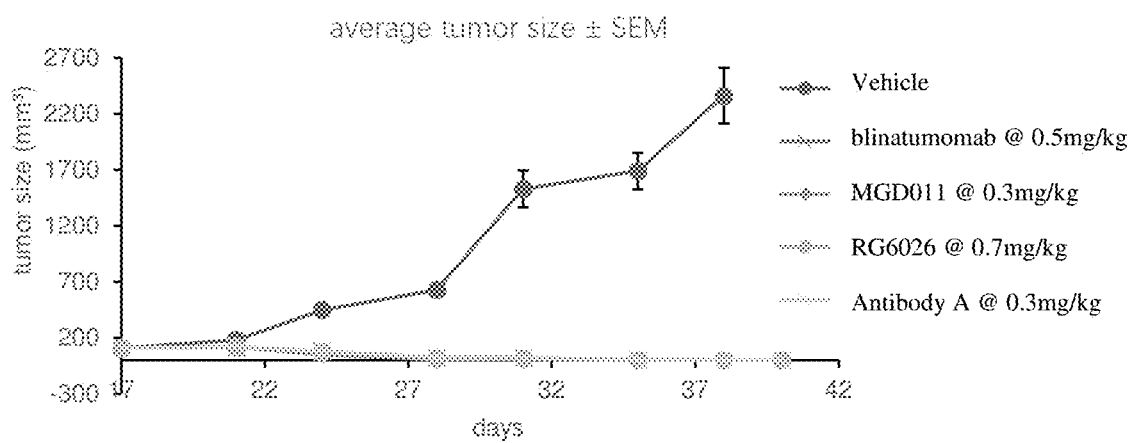
FIG. 3 depicts inhibition effect of antibody A as described herein on tumor.
Figure 4:
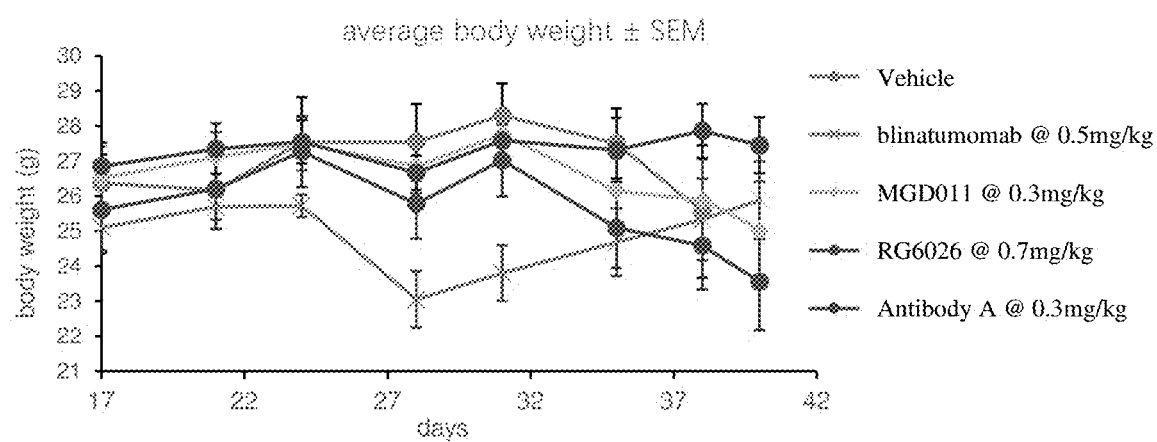
FIG. 4 depicts the effect of antibody A as described herein on mice body weight.
Figure 5:
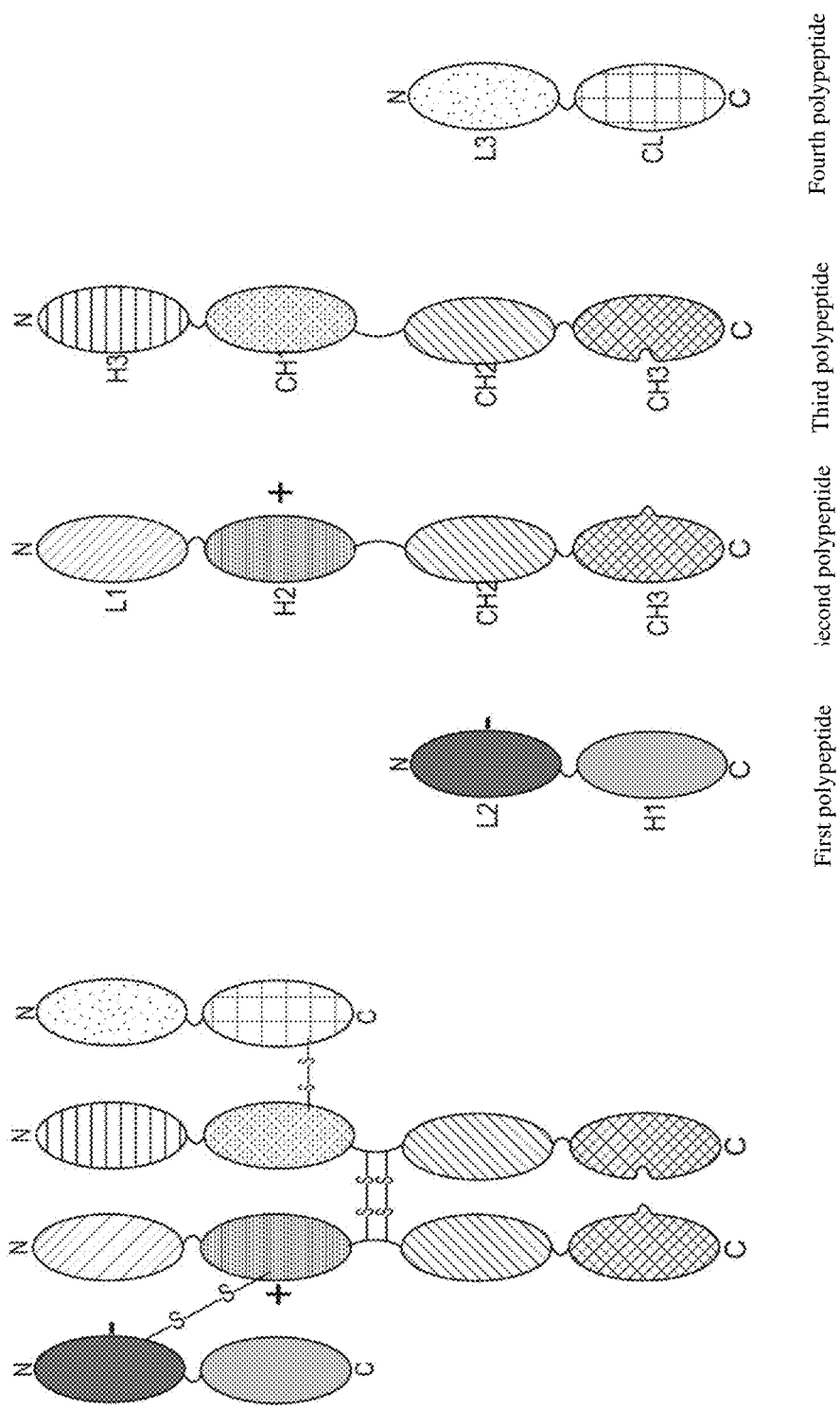
FIG. 5 is the structure diagram of the tri-specific antibody according to one embodiment as described herein.

The experiment ended 40 days after inoculation. All treatment (antibody) groups showed significant inhibition on tumor growth (as shown in FIG. 3). All treatment (antibody) groups showed no significant weight loss (as shown in FIG. 4), which means all antibodies for treatment had no significant in vivo toxicity.

Example 4. Constructions of Tri-Specific Antibody

This example illustratively describes the method for constructing a CD3×CD19×CD20 tri-specific antibody. In the construction of the tri-specific antibody, the amino acid sequences of VH and VL of CD3, CD19 and CD20 are listed in SEQ ID NOs.: 1 to 4 and SEQ ID NOs.: 8 and 9 (CD3 VL: SEQ ID NO.:1, CD3 VH: SEQ ID NO.:2, CD19 VL: SEQ ID NO.:3, CD19 VH: SEQ ID NO.:4, CD20 VL: SEQ ID NO.:8, CD20 VH: SEQ ID NO.:9).

According to the construction method as described in Example 1, the CD3×CD19×CD20 tri-specific antibody (antibody #1) with four polypeptide chains as shown below was constructed.

```
Polypeptide A (SEQ ID NO.: 10):
CD19 VL-linker-CD3 VH

Polypeptide B (SEQ ID NO.: 11):
CD3 VL-linker-CD19 VH-hinge-CH2CH3
```

-continued

```
Polypeptide C (SEQ ID NO.: 12):
CD20 VH-CH1-hinge-CH2CH3

Polypeptide D (SEQ ID NO.: 13):
CD20 VL-CL
```

By using the same construction method as mentioned above, a CD3×CD19×CD20 tri-specific antibody (antibody #2) was constructed, in which the positions of CD3, CD19 and CD20 were exchanged. This tri-specific antibody comprised four polypeptide chains as below.

```
Polypeptide E (SEQ ID NO.: 14):
CD19 VL-linker-CD20 VH

Polypeptide F (SEQ ID NO.: 15):
CD20 VL-linker-CD19 VH-hinge-CH2CH3

Polypeptide G (SEQ ID NO.: 16):
CD3 VH-CH1-hinge-CH2CH3

Polypeptide H (SEQ ID NO.: 17):
CD3 VL-CL
```

The antibodies #1 and #2 were purified by Size Exclusion with purity above 90%.

Example 5 Affinity Assay

The affinity of antibody #1 for human CD3E antigen and human CD19 antigen was tested by using BIAcore method. ka, kd and KD values were calculated from the experimental results and used to evaluate affinity. Human CD19 as ligands was immobilized to chips conjugated with anti-histine antibodies. Sample antibodies, at 5 different concentrations, were injected to the system to be analyzed. Human CD3E antigen and human CD19 antigen were immobilized to the chip to assay affinity of antibody A by using BIAcore method. The results were listed as below.

| Antigen | ka (1/Ms) | kd (1/s) | KD (M) |
|---|---|---|---|
| CD3 | 3.342E+5 | 0.008349 | 2.498E−8 |
| CD19 | 2.068E+5 | 2.727E−4 | 1.319E−9 |

Example 6. Cell Killing Assays on Raji Cells

Antibody-mediated killing effect on target cells (Raji cells) was assayed using lymphocytes as effector cells. Protocol as described below.

Preparation of effector cells: Peripheral blood mononuclear cells (PBMCs) were freshly separated from blood through density gradient centrifugation, and CD4+T cells and CD8+T cells were further separated from PBMCs by using Stemcell separation kit. PBMCs, CD4+T cells and CD8+T cells were respectively re-suspended in cell culture medium and cell density and cell survival rate were examined. Cell culture medium was used to adjust cell density to $6 \times 10^6$ live cells/mL before 50 μL per well of cell suspension was added to flat-bottom 96-well plates. Effector cells to target cells ratio (Eff) was 20:1 for the experiments. The cell culture medium was RPMI 1640 in which 10% HI-FBS and 1% Penicillin & Streptomycin were suspended.

Preparation of target cells: Raji cells were passed at $2 \times 10^5$ cells/mL and used for experiments 4 days after passage. Proper amount of cell suspension was transferred to 50 ml tubes and centrifuged for 5 minutes at 200 g, room temperature. Cells were re-suspended with cell culture medium and examined for cell density and cell survival rate. Cell culture medium was used to adjust cell density to $3 \times 10$ live cells/mL before 50 μL per well of cell suspension was added to flat-bottom 96-well plates with Raji cells already in.

Preparation of antibodies: The antibodies #1 and #2 and bispecific antibody CD3×CD19 as control were diluted to different concentrations in the cell culture medium. 50 μL cell culture medium or diluted solution were added to the indicated wells to arrive at final concentration 0 pM, 1 pM or 100 pM.

Figure 6:
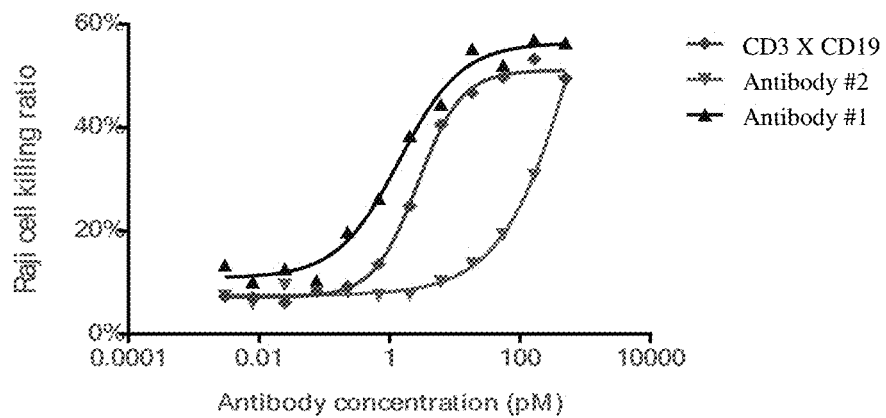
FIG. 6 depicts the killing effect of antibodies #1 and #2 as described herein on Raji cells.

The 96-well plates with antibodies, target cells and effector cells were placed into an incubator at 37° C. and 5% $CO_2$. At 4-hour point, 20-hour point and 40-hour point, the samples were collected for examination. The samples were centrifuged for 5 minutes at 350 g. The cells were resuspended and stained with PI. 10 μL counting beads were added to each well before conducting flow cytometry. The results showed that antibody #2 had a EC50 value of 971.8 pM, antibody #1 had a EC50 value of 1.423 pM. The killing effect of antibodies #1 and #2 on target cells was shown in FIG. 6.

Example 7. Cell Killing Effect on K562 Cells

In order to observe the cell killing effect of CD3×CD19×CD20 which is independent of CD19, K562 cells that were double negative for CD19 and CD20 were stably transfected with CD20 to be used as target cells and the lymphocytes were used as effector cells so as to evaluate the antibody-induced killing effect on target cells (K562 cells).

Figure 7:
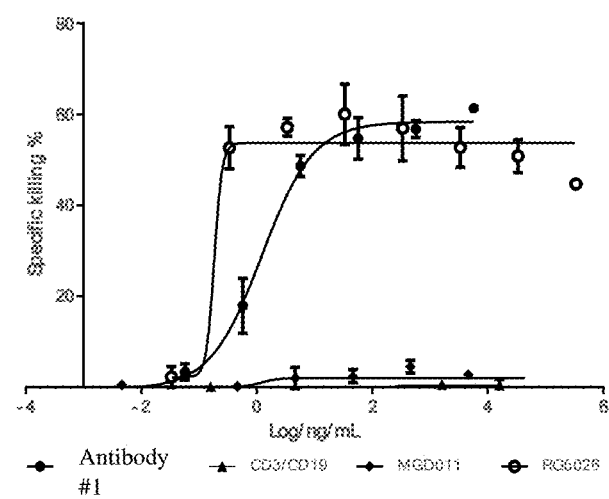
FIG. 7 depicts the killing effect of antibodies #1 and #2 as described herein on K562 cells.

K562-CD20 cells were re-suspended in 1640 culture medium with 2% FBS and then were centrifuged for 5 min at 1000 rpm to conduct counting. The K562-CD20 cells were inoculated into a 96-well plate at a concentration of 10000 cells/100 ul. PBMCs were centrifuged for 5 min at 1000 rpm and then re-suspended into 1640 culture medium with 2% FBS. Such treated PBMCs were added into the above-mentioned %-well plate at a concentration of 100000 cells/100 ul. PBS was used to dilute the antibody. 1 in 10 dilutions for 8 concentrations. 10 ul dilution was added to each well, in duplicates. The %-well plate was placed into an incubator at 37° C. and 5% $CO_2$ for 4 h. A substrate from a kit was resuspended in 12 ml buffer. The %-well plate was centrifuged for 5 min at 1500 rpm and then 50 uL supernatant was collected from each well and transferred to a new 96-well plate. For this new %-well plate, 50 uL diluted substrate as mentioned above was also added to each well. This plate was incubated for 10 min in dark. ELISA was used to detect absorbance at OD490. The antibody #1 had a EC50 value of 1.222 pM and the killing effect of antibody #1 and control antibody was shown in FIG. 7.

Example 8. Evaluation of In Vivo Efficiency

Antibodies #1 and #2 were tested for their in vivo anti-tumor effect in Jeko-1/NCG Mixeno model. On the starting day (Day 0), $5 \times 10^6$ Jeko-1 cells suspended in 100 μL 1:1 PBS/gel was inoculated in the right flank of animals. 3 days after inoculation (Day 3) $1 \times 10^7/0.1$ mL PBMC were injected into the abdomen of animals. Sample antibodies #1 and #2 were administrated when average tumor size reached 100 mm³. 4 antibodies were tested (CD3×CD19@0.5 mg/kg, antibody #1@0.5 mg/kg, antibody #1@0.3 mg/kg, and antibody #2@0.5 mg/kg) together with one pH6.0 PBS control group; 6 animals per group. All samples were administrated by intravenous injection into the caudal vein. All antibodies and the vehicle were administrated twice a week for 3 weeks consecutively. Effect was evaluated based on relative tumor inhibition (TGIRTV), and safety was evaluated on animal weight change and animal death.

Relative tumor growth inhibition rate TGIRTV (%): TGIRTV=1-TRTV/CRTV(%). TRTV/CRTV(%) is relative tumor growth rate, i.e. at a certain time point, the ratio between the tumor volume of the group that received treatment to the tumor volume of the control group that received PBS. TRTV and CRTV are tumor volume (TV) of the treatment group and the control group at a certain time point, respectively.

The experiment ended 40 days after inoculation. All treatment (antibody) groups showed significant inhibition on tumor growth (as shown in FIG. 9). All treatment (antibody) groups showed no significant weight loss (as shown in FIG. 8), which means all antibodies for treatment had no significant in vivo toxicity.

The present description is described in details by referring to the specific examples. These examples are merely illustrative, but not intend to limit the scope of the present invention. One having the ordinary skill in the art would understand that various modifications, changes or substitutions may be made without departing from the spirit of the present invention. Thus, all equivalent variations according to the present description fall within the scope of the present description.

```
                         SEQUENCE LISTING

Sequence total quantity: 21
SEQ ID NO: 1            moltype = AA  length = 109
FEATURE                 Location/Qualifiers
REGION                  1..109
                        note = CD3 VL amino acid sequence
source                  1..109
                        mol_type = protein
                        organism = synthetic construct
SEQUENCE: 1
QAVVTQEPSL TVSPGGTVTL TCRSSTGAVT TSNYANWVQD KPGQAPRGLI GGTNKRAPWT  60
PARFSGSLLG GKAALTITGA QPEDEAEYYC ALWYSNLWVF GGGTKLTVL            109

SEQ ID NO: 2            moltype = AA  length = 126
FEATURE                 Location/Qualifiers
REGION                  1..126
                        note = CD3 VH amino acid sequence
source                  1..126
                        mol_type = protein
                        organism = synthetic construct
SEQUENCE: 2
EVQLVESGGG LVQPGGSLRL SCAASGFTFN TYAMNWVRQA PGKGLEWVGR IRSKYNNYAT  60
YYADSVDKGR FTISRDDSKN SLYLQMNSLK TEDTAVYYCV RHGNFGNSYV SWFAYWGQGT 120
LVTVSS                                                           126

SEQ ID NO: 3            moltype = AA  length = 107
FEATURE                 Location/Qualifiers
REGION                  1..107
                        note = CD19 VL amino acid sequence
source                  1..107
                        mol_type = protein
                        organism = synthetic construct
SEQUENCE: 3
EIVLTQSPAT LSVTPGERAT LSCSASSSVS YMHWYQQKPG QAPRLLIYDT SKLASGIPAR  60
FSGSGSGTDF TLTISSLEPE DFAVYYCFQG SVYPFTFGQG TKLEIKR              107

SEQ ID NO: 4            moltype = AA  length = 120
FEATURE                 Location/Qualifiers
REGION                  1..120
                        note = CD19 VH amino acid sequence
source                  1..120
                        mol_type = protein
                        organism = synthetic construct
SEQUENCE: 4
QVQLQESGPG LVKPSQTLSL TCTVSGGSIS TSGMGVGWIR QHPGKGLEWI GHIWWDDDKR  60
YNPALKSRVT ISVDTSKNQF SLKLSSVTAA DTAVYYCARM ELWSYYFDYW GQGTTLTVSS 120

SEQ ID NO: 5            moltype = AA  length = 237
FEATURE                 Location/Qualifiers
REGION                  1..237
                        note = Synthetic: amino acid sequence of the first
                         polypeptide
source                  1..237
                        mol_type = protein
                        organism = synthetic construct
SEQUENCE: 5
EIVLTQSPAT LSVTPGERAT LSCSASSSVS YMHWYQKKPG QAPRLLIYDT SKLASGIPAR  60
FSGSGSGTDF TLTISSLEPE DFAVYYCFQG SVYPFTFGCG TKLEIKRTVA AEVQLVESGG 120
GLVQPGGSLR LSCAASGFTF NTYAMNWVRK APGKGLEWVG RIRSKYNNYA TYYADSVDKG 180
```

```
RFTISRDDSK NSLYLQMNSL KTEDTAVYYC VRHGNFGNSY VSWFAYWGQG TLVTVSS       237

SEQ ID NO: 6              moltype = AA   length = 467
FEATURE                   Location/Qualifiers
REGION                    1..467
                          note = Synthetic: amino acid sequence of the second
                           polypeptide
source                    1..467
                          mol_type = protein
                          organism = synthetic construct
SEQUENCE: 6
EAVVTQEPSL TVSPGGTVTL TCRSSTGAVT TSNYANWVQD KPGQAPRGLI GGTNKRAPWT     60
PARFSGSLLG GKAALTITGA QPEDEAEYYC ALWYSNLWVF GGGTKLTVLR TVAAQVQLQE    120
SGPGLVKPSQ TLSLTCTVSG GSISTSGMGV GWIRDHPGKC LEWIGHIWWD DDKRYNPALK    180
SRVTISVDTS KNQFSLKLSS VTAADTAVYY CARMELWSYY FDYWGQGTTL TVSSASEPKS    240
DKTHTCPPCP APPVAGGPSV FLFPPKPKDT LMISRTPEVT CVVVDVSQED PEVKFNWYVD    300
GVEVHNAKTK PREEQFNSTY RVVSVLTVLH QDWLNGKEYK CKVSNKGLPS SIEKTISKAK    360
GQPREPQVYT LPPCRDELTK NQVSLWCLVK GFYPSDIAVE WESNGQPENN YKTTPPVLDS    420
DGSFFLYSKL TVDKSRWQQG NVFSCSVMHE ALHNHYTQKS LSLSPGK                 467

SEQ ID NO: 7              moltype = AA   length = 227
FEATURE                   Location/Qualifiers
REGION                    1..227
                          note = Synthetic: amino acid sequence of the third
                           polypeptide
source                    1..227
                          mol_type = protein
                          organism = synthetic construct
SEQUENCE: 7
DKTHTCPPCP APPVAGGPSV FLFPPKPKDT LMISRTPEVT CVVVDVSQED PEVKFNWYVD     60
GVEVHNAKTK PREEQFNSTY RVVSVLTVLH QDWLNGKEYK CKVSNKGLPS SIEKTISKAK    120
GQPREPQVCT LPPSRDELTK NQVSLSCAVK GFYPSDIAVE WESNGQPENN YKTTPPVLDS    180
DGSFFLVSKL TVDKSRWQQG NVFSCSVMHE ALHNRFTQKS LSLSPGK                 227

SEQ ID NO: 8              moltype = AA   length = 112
FEATURE                   Location/Qualifiers
REGION                    1..112
                          note = CD20 VL amino acid sequence
source                    1..112
                          mol_type = protein
                          organism = synthetic construct
SEQUENCE: 8
DIVMTQTPLS LPVTPGEPAS ISCRSSKSLL HSNGITYLYW YLQKPGQSPQ LLIYQMSNLV     60
SGVPDRFSGS GSGTDFTLKI SRVEAEDVGV YYCAQNLELP YTFGGGTKVE IK            112

SEQ ID NO: 9              moltype = AA   length = 119
FEATURE                   Location/Qualifiers
REGION                    1..119
                          note = CD20 VH amino acid sequence
source                    1..119
                          mol_type = protein
                          organism = synthetic construct
SEQUENCE: 9
QVQLVQSGAE VKKPGSSVKV SCKASGYAFS YSWINWVRQA PGQGLEWMGR IFPGDGDTDY     60
NGKFKGRVTI TADKSTSTAY MELSSLRSED TAVYYCARNV FDGYWLVYWG QGTLVTVSS    119

SEQ ID NO: 10             moltype = AA   length = 236
FEATURE                   Location/Qualifiers
REGION                    1..236
                          note = Synthetic: amino acid sequence of the first
                           polypeptide
source                    1..236
                          mol_type = protein
                          organism = synthetic construct
SEQUENCE: 10
EIVLTQSPAT LSVTPGERAT LSCSASSSVS YMHWYQKKPG QAPRLLIYDT SKLASGIPAR     60
FSGSGSGTDF TLTISSLEPE DFAVYYCFQG SVYPFTFGCG TKLEIKRTVA AEVQLVESGG    120
GLVQPGGSLR LSCAASGFTF STYAMNWVRQ APGKGLEWVG RIRSKYNNYA TYYADSVKGR    180
FTISRDDSKN SLYLQMNSLR AEDTAVYYCV RHGNFGNSYV SWFAYWGQGT LVTVSS       236

SEQ ID NO: 11             moltype = AA   length = 465
FEATURE                   Location/Qualifiers
REGION                    1..465
                          note = Synthetic: amino acid sequence of the second
                           polypeptide
source                    1..465
                          mol_type = protein
                          organism = synthetic construct
SEQUENCE: 11
```

```
QAVVTQEPSL TVSPGGTVTL TCRSSTGAVT TSNYANWVQQ KPGQAPRGLI GGTNKRAPWT    60
PARFSGSLLG GKAALTLSGA QAEDEADYYC ALWYSNLWVF GGGTKLTVLR TVAAQVQLQE   120
SGPGLVKPSQ TLSLTCTVSG GSISTSGMGV GWIRDHPGKC LEWIGHIWWD DDKRYNPALK   180
SRVTISVDTS KNQFSLKLSS VTAADTAVYY CARMELWSYY FDYWGQGTTL TVSSASEPKS   240
SDKTHTCPPC PAPPVAGPSV FLFPPKPKDT LMISRTPEVT CVVVDVSQED PEVKFNWYVD   300
GVEVHNAKTK PREEQFNSTY RVVSVLTVLH QDWLNGKEYK CKVSNKGLPS SIEKTISKAK   360
GQPREPQVYT LPPSRDELTK NQVSLWCLVK GFYPSDIAVE WESNGQPENN YKTTPPVLDS   420
DGSFFLYSKL TVDKSRWQQG NVFSCSVMHE ALHNHYTQKS LSLSP                  465

SEQ ID NO: 12           moltype = AA  length = 446
FEATURE                 Location/Qualifiers
REGION                  1..446
                        note = Synthetic: amino acid sequence of the third
                        polypeptide
source                  1..446
                        mol_type = protein
                        organism = synthetic construct
SEQUENCE: 12
QVQLVQSGAE VKKPGSSVKV SCKASGYAFS YSWINWVRQA PGQGLEWMGR IFPGDGDTDY    60
NGKFKGRVTI TADKSTSTAY MELSSLRSED TAVYYCARNV FDGYWLVYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPPVAGPS   240
VFLFPPKPKD TLMISRTPEV TCVVVDVSQE DPEVKFNWYV DGVEVHNAKT KPREEQFNST   300
YRVVSVLTVL HQDWLNGKEY KCKVSNKGLP SSIEKTISKA KGQPREPQVY TLPPSRDELT   360
KNQVSLSCAV KGFYPSDIAV EWESNGQPEN NYKTTPPVLD SDGSFFLVSK LTVDKSRWQQ   420
GNVFSCSVMH EALHNRFTQK SLSLSP                                       446

SEQ ID NO: 13           moltype = AA  length = 219
FEATURE                 Location/Qualifiers
REGION                  1..219
                        note = Synthetic: amino acid sequence of the fourth
                        polypeptide
source                  1..219
                        mol_type = protein
                        organism = synthetic construct
SEQUENCE: 13
DIVMTQTPLS LPVTPGEPAS ISCRSSKSLL HSNGITYLYW YLQKPGQSPQ LLIYQMSNLV    60
SGVPDRFSGS GSGTDFTLKI SRVEAEDVGV YYCAQNLELP YTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 14           moltype = AA  length = 234
FEATURE                 Location/Qualifiers
REGION                  1..234
                        note = Synthetic: amino acid sequence of the first
                        polypeptide
source                  1..234
                        mol_type = protein
                        organism = synthetic construct
SEQUENCE: 14
EIVLTQSPAT LSVTPGERAT LSCSASSSVS YMHWYQDKPG QAPRLLIYDT SKLASGIPAR    60
FSGSGSGTDF TLTISSLEPE DFAVYYCFQG SVYPFTFGCG TKLEIKGGSG GSGGGSQVQLV  120
QSGAEVKKPG SSVKVSCKAS GYAFSYSWIN WVRQAPGQGL EWMGRIFPGD GDTDYNGKFK   180
GRVTITADKS TSTAYMELSS LRSEDTAVYY CARNVFDGYW LVYWGQGTLV TVSS          234

SEQ ID NO: 15           moltype = AA  length = 471
FEATURE                 Location/Qualifiers
REGION                  1..471
                        note = Synthetic: amino acid sequence of the second
                        polypeptide
source                  1..471
                        mol_type = protein
                        organism = synthetic construct
SEQUENCE: 15
DIVMTQTPLS LPVTPGEPAS ISCRSSKSLL HSNGITYLYW YLQKPGQSPQ LLIYQMSNLV    60
SGVPDRFSGS GSGTDFTLKI SRVEAEDVGV YYCAQNLELP YTFGGGTKVE IKGGSGGSGG   120
SQVQLQESGP GLVKPSQTLS LTCTVSGGSI STSGMGVGWI RKHPGKCLEW IGHIWWDDDK   180
RYNPALKSRV TISVDTSKNQ FSLKLSSVTA ADTAVYYCAR MELWSYYFDY WGQGTTLTVS   240
SASEPKSDKT HTCPPCPAPP VAGPSVFLFP PKPKDTLMIS RTPEVTCVVV DVSQEDPEVK   300
FNWYVDGVEV HNAKTKPREE QFNSTYRVVS VLTVLHQDWL NGKEYKCKVS NKGLPSSIEK   360
TISKAKGQPR EPQVYTLPPS RDELTKNQVS LWCLVKGFYP SDIAVEWESN GQPENNYKTT   420
PPVLDSDGSF FLYSKLTVDK SRWQQGNVFS CSVMHEALHN HYTQKSLSLS P            471

SEQ ID NO: 16           moltype = AA  length = 450
FEATURE                 Location/Qualifiers
REGION                  1..450
                        note = Synthetic: amino acid sequence of the third
                        polypeptide
source                  1..450
```

```
                        mol_type = protein
                        organism = synthetic construct
SEQUENCE: 16
EVQLVESGGG LVQPGGSLRL SCAASGFTFS TYAMNWVRQA PGKGLEWVGR IRSKYNNYAT    60
YYADSVKGRF TISRDDSKNS LYLQMNSLKT EDTAVYYCVR HGNFGNSYVS WFAYWGQGTL   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPPV   240
AGPSVFLFPP KPKDTLMISR TPEVTCVVVD VSQEDPEVKF NWYVDGVEVH NAKTKPREEQ   300
FNSTYRVVSV LTVLHQDWLN GKEYKCKVSN KGLPSSIEKT ISKAKGQPRE PQVYTLPPSR   360
DELTKNQVSL SCAVKGFYPS DIAVEWESNG QPENNYKTTP PVLDSDGSFF LVSKLTVDKS   420
RWQQGNVFSC SVMHEALHNR FTQKSLSLSP                                    450

SEQ ID NO: 17           moltype = AA  length = 216
FEATURE                 Location/Qualifiers
REGION                  1..216
                        note = Synthetic: amino acid sequence of the fourth
                         polypeptide
source                  1..216
                        mol_type = protein
                        organism = synthetic construct
SEQUENCE: 17
QAVVTQEPSL TVSPGGTVTL TCRSSTGAVT TSNYANWVQQ KPGQAPRGLI GGTNKRAPWT    60
PARFSGSLLG GKAALTITGA QAEDEADYYC ALWYSNLWVF GGGTKLTVLR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 18           moltype = AA  length = 5
FEATURE                 Location/Qualifiers
REGION                  1..5
                        note = Synthetic: sequence of the linker
source                  1..5
                        mol_type = protein
                        organism = synthetic construct
SEQUENCE: 18
RTVAA                                                                 5

SEQ ID NO: 19           moltype = AA  length = 5
FEATURE                 Location/Qualifiers
REGION                  1..5
                        note = Synthetic: sequence of the linker
source                  1..5
                        mol_type = protein
                        organism = synthetic construct
SEQUENCE: 19
GGGGS                                                                 5

SEQ ID NO: 20           moltype = AA  length = 6
FEATURE                 Location/Qualifiers
REGION                  1..6
                        note = Synthetic: sequence of the linker
source                  1..6
                        mol_type = protein
                        organism = synthetic construct
SEQUENCE: 20
GGSGGS                                                                6

SEQ ID NO: 21           moltype = AA  length = 9
FEATURE                 Location/Qualifiers
REGION                  1..9
                        note = Synthetic: sequence of the linker
source                  1..9
                        mol_type = protein
                        organism = synthetic construct
SEQUENCE: 21
GGSGGSGGS                                                             9
```

The invention claimed is:

1. An engineered multi-specific antibody that bins to CD3, CD19 and CD20, and comprises:
   (i) a first polypeptide comprising the amino acid sequence set forth in SEQ ID NO: 10;
   (ii) a second polypeptide comprising the amino acid sequence set forth in SEQ ID NO: 11,
   (iii) a third polypeptide comprising the amino acid sequence of set forth in SEQ ID NO: 12; and
   (iv) a fourth polypeptide comprising the amino acid sequence set forth in SEQ ID NO: 13.

* * * * *